(12) United States Patent
Frentsch et al.

(10) Patent No.: US 7,659,084 B2
(45) Date of Patent: Feb. 9, 2010

(54) METHODS FOR DETECTING AND ISOLATING ANTIGEN-SPECIFIC T LYMPHOCYTES WITH CD40/C154 INHIBITORS

(75) Inventors: Marco Frentsch, Berlin (DE); Martin Rothe, Berlin (DE); Andreas Thiel, Berlin (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 408 days.

(21) Appl. No.: 10/525,238

(22) PCT Filed: Aug. 22, 2003

(86) PCT No.: PCT/EP03/09354

§ 371 (c)(1),
(2), (4) Date: Oct. 12, 2005

(87) PCT Pub. No.: WO2004/027428

PCT Pub. Date: Apr. 1, 2004

(65) Prior Publication Data

US 2006/0121027 A1 Jun. 8, 2006

(30) Foreign Application Priority Data

Aug. 23, 2002 (EP) .................. 02090300

(51) Int. Cl.
*G01N 33/53* (2006.01)
*C12N 5/08* (2006.01)
(52) U.S. Cl. .............. 435/7.24; 435/7.1; 435/7.2; 435/7.21; 435/375; 435/377
(58) Field of Classification Search ............ None
See application file for complete search history.

(56) References Cited

U.S. PATENT DOCUMENTS 6,576,428 B1 6/2003 Assenmacher et al.
2003/0012781 A1* 1/2003 Darrell et al. ............ 424/131.1

FOREIGN PATENT DOCUMENTS

WO  WO 9958977  11/1999

OTHER PUBLICATIONS

Batataglia et al., Am. J. Gastroenterology 94: 3279-3284, 1999.*

XP002937171—Berner et al.; "Increased expression of CD40 ligand (CD154) on CD4+ T cells as a marker of disease activity in rheumatoid arthritis"; Nov. 1999; pp. 190-195.
XP001053568—Schonbeck et al.; "Molecules in focus"; The International Journal of Biochemistry & Cell Biology, vol. 32 , 2000; pp. 687-693.
Fisher et al.; "Immunomagnetic separation reagents as markers in electron microscopy"; Journal of Immunological Methods; vol. 262, 2002; pp. 95-101.
XP000887155— Valmori et al.; "An Antigen-targeted Approach to Adoptive Transfer Therapy of Cancer"; Cancer Research, vol. 59, May 1999; pp. 2167-2173.
XP002220000; Lee et al.; "The biological outcome of CD40 signaling in B lymphocytes is dependent on the duration of CD154 expression on T cells: Reciprocal regulation by IL-4 and IL-12"; FASEB Journal; Mar., 2002; 1 p.
Berner et al: "Increased Expression of CD40 Ligand (CD154) on CD4+ T Cells as a Marker of Disease Activity in Rheumatoid Arthritis" Annals of the Rheumatic Diseases, British Medical Association, London, GB, vol. 59, 2000, pp. 190-195.
Schoenbeck U et al: "CD154 (CD40 Ligand)" International Journal of Biochemistry and Cell Biology, Exeter, GB, vol. 32, No. 7, Jul. 2000, pp. 687-693.
Fisher P J et al. "Immunomagnetic Separation Reagents as Markers in Electron Microscopy" Journal of Immunological Methods, Elsevier, Amsterdam, NL, vol. 262, No. 1-2, Apr. 1, 2002, pp. 95-101.
Database Biosis 'Online! Biosciences Inforamtion Service, Philadelphia, PA, US; Mar. 20, 2002, Lee Byung O et al.: "The Biological Outcome of CD40 Signaling in B Lymphocytes is Dependent on the Duration of CD154 Expression on T Cells: Reciprocal Regulation by IL-4 and IL-12."
FASEB Journal, vol. 16, No. 4, Mar. 20, 2002, p. A350, Annual Meeting of the Professional Research Scientists on Experimental Biology; New Orleans, Louisiana, USA; Apr. 20-24, Mar. 20, 2002.
Valmori D et al: "Antigen-Targeted Approach to Adoptive Transfer Therapy of Cancer" Cancer Research, American Association for Cancer Research, Baltimore, MD, vol. 59, No. 9, 1999, pp. 2167-2173.

* cited by examiner

*Primary Examiner*—Phillip Gambel
(74) *Attorney, Agent, or Firm*—Millen, White, Zelano, Branigan, P.C.

(57) ABSTRACT

What is suggested herein is the use of CD154 for the detection and/or isolation of antigen-specific T lymphocytes and a method for the detection and/or isolation of antigen-specific T lymphocytes, wherein the suspension is contacted with a CD40/CD154 system inhibitor, intra- or extracellular determination of CD154 is effected, and the cells having CD154 are detected and/or isolated.

16 Claims, 3 Drawing Sheets

METHODS FOR DETECTING AND ISOLATING ANTIGEN-SPECIFIC T LYMPHOCYTES WITH CD40/C154 INHIBITORS

This application is a National Stage application under §371 of PCT/EP03/09354, filed Aug. 22, 2003 and claims priority to European application No. EP 02090300.1, filed Aug. 23, 2002.

The invention relates to the use of CD154 for the detection and isolation of T lymphocytes recognizing a defined antigen and to a method for the detection and isolation of T lymphocytes in cell suspensions or body fluids, which T lymphocytes recognize a defined antigen.

The immune system is constituted of cells and molecules circulating in the body, the homeostasis and cooperation thereof being balanced by cytokines and growth factors. Cells not being required are eliminated by apoptosis. These mechanisms are affected by external influences or by genetic predispositions of a variety of types. The immune system plays a key role in the development of many diseases, especially allergies, inflammations and autoimmune diseases. It is responsible for enhanced immunity following vaccinations, but fails when the development of tumor diseases is concerned.

Dendritic cells (DC) are the safeguards of the immune system, being located at sites in the body where foreign and potentially hazardous substances might invade. They are professional antigen-presenting cells which receive and digest the antigen, present peptide fragments of the antigen to specific T lymphocytes, thereby activating the latter. The immature precursors of DCs continuously migrate through the blood and into the lymphatic organs where they undergo differentiation into mature DCs under particular circumstances. There are various precursor cells capable of maturing into different types of DCs. Also, these different types of DCs respond differently to antigens by expressing specific membrane molecules and cytokines, thereby controlling the activation of the T lymphocytes which then may become pro-(Th1) or anti-inflammatory (Th2), regulatory (Tr) or tolerant (Ta). The type of T lymphocyte activation is determined by co-stimulatory activation signals from antigen-presenting cells. Activation signals are represented by ligands for receptors of T lymphocytes. Said ligands are situated on the surface of the APCs, they are bound to the extracellular matrix or secreted by cells, as are the cytokines. However, in addition to antigen-specific activation by signals via the antigen receptor of the T lymphocytes and co-stimulating ligands, non-specific activation of T lymphocytes has also been described, e.g. via cytokines or lectins.

However, the elucidation of all molecular changes during the activation reaction and functional differentiation of T lymphocytes is still incomplete as yet. Similarly, the detection of the states of activation and function of T lymphocytes recognizing a specific antigen is only possible with some imprecision with the present state of the art.

For clinical uses in the diagnosis of diseases, as well as in research, it is essential to be capable of detecting particularly those specific T lymphocytes which can be activated by a particular antigen. Furthermore, it would be desirable to be capable of isolating such antigen-specific T lymphocytes from cell mixtures, especially for cell-therapeutic purposes.

Several prior art methods allowing determination of the states of activation and function of T lymphocytes have been disclosed. Thus, DE 100 21 834 A1 discloses mRNA molecules for use as indicators of the functional state of T lymphocytes, said mRNA molecules in the event of activated T lymphocytes being expressed to a greater or lesser extent compared to the normal or inactive state. By determining the interaction between the complementary, hybridized nucleic acid sequences, it is possible to determine the differences in the expression levels of the mRNA molecules, thereby allowing conclusions as to the state of activation of the T lymphocytes. Furthermore, the above printed document discloses the use of polypeptides encoded by said nucleotide sequences, antibodies directed against said polypeptides, as well as the use of said antibodies to detect the states of activation and function of T lymphocytes.

DE 37 37 703 A1 discloses antibodies directed against a neutrophilically activating polypeptide, which antibodies can be used as diagnostic agent to detect and characterize activated structures of a cellular immune response.

DE 42 26 974 C2 discloses a method and device for the treatment and separation of cell suspensions. The described separation device and method for the continuous treatment of a cell suspension can be used to separate different components, e.g. of human blood, thereby allowing specific purification of cells associated with the cellular immune response.

U.S. Pat. No. 5,874,302 discloses a method wherein T lymphocytes are cultured and the T lymphocytes thus obtained are used in clinical treatments of tumors. According to the above U.S. Pat. No. 5,874,302, blood is used as starting material for the preparation of a T cell culture suspension, the corresponding starting material being co-cultured with particular tumor cells.

CA 1,296,622 discloses a method and a device for the determination of the immunoregulatory state of leukocytes. The leukocytes are stimulated with standard substances to determine the immunoregulatory state, using labelled antibodies, for example. To this end, a sample of peripheral mononuclear cells from a patient having received an immune-influencing agent is grown at first, and thereafter, the percentage of mononuclear cells expressing an activation antigen in vitro is determined in an aliquot of the grown sample. Subsequently, this percentage is compared with a predetermined value of the percentage as an indication of the in vitro effect, thereby allowing determination of the immunoregulatory state of the patient or of the effect of the immune-influencing therapy on the immunoregulatory state. Subclasses of the mononuclear cells to be determined include T lymphocytes, cytotoxic T lymphocytes and helper T lymphocytes, for example.

WO 99/58977 describes a method for the direct selection of antigen-specific T lymphocytes. Therein, the T lymphocytes are separated via production of cytokines, using flow cytometry or magnetic cell sorting. In this case, activated T lymphocytes are selected which express one or more particular cytokines following stimulation with antigen.

Furthermore, distinguishing activation by a viral or bacterial infection from activation by an autoimmune reaction or by transplant rejection is not possible by means of known diagnostic methods, although such differentiation would be desirable from a diagnostic and a clinical point of view. Due to the inadequate detection of activated T lymphocytes in a biological sample, specific separation of such cells is not possible either, because this would require initial unambiguous determination thereof.

To date, no immunodiagnostic methods have been described that would allow rapid and easy detection of the entire antigen-specific T lymphocytes and their isolation as well. In a variety of diseases, direct antigen-specific detection of the T lymphocytes assuming central control of the immune responses and thus, of a variety of immunopathogeneses, or their isolation for use in cell-therapeutic approaches, such as adoptive T cell transfer, is of utmost diagnostic and therapeutic interest. This includes diseases such as allergies and autoimmune diseases resulting from miscontrolled immune reactions, as well as chronic infectious diseases, tumors or leucemias.

Current methods are based on two different strategies:

(i) "Structural" detection of antigen-specific T lymphocytes is based on direct labelling of T cell receptors developed by the T lymphocytes, using MHC multimers complexed together with the respective antigenic peptides (U.S. Pat. No. 5,635,363/FR 9911133). The drawbacks of such methods are to be seen in the fact that, on the one hand, they depend on the MHC genotype developed by the individual to be investigated, and, on the other hand, that the MHC molecules undergo complexing with only one immunodominant peptide epitope of the respective antigen. Consequently, each agent has to be produced individually, in accordance with the genotype and the antigen's immunodominant peptide epitope which, in addition, is known in only a few antigens and for only, a few MHC alleles, Moreover, due to specific structural features of the MHC-II molecule, the production of MHC-II multimers essential for the detection and isolation of MHC-II-restricted antigen-specific CD4+ Th lymphocytes with a quality sufficient for use has not been possible as yet.

(ii) Functional detection of antigen-specific T lymphocytes is based either on antigen-reactive proliferation after stimulation with antigen, which, however, can only be detected after 3-5 days, or on antigen-reactive expression of activation molecules or secretion of cytokines. While part of the activation markers described so far are also formed by particular non-activated T lymphocytes, thus being insufficiently specific, it is not possible to detect the entire specific T lymphocytes via "reactive" expression of cytokines. Thus, due to the inadequate detection of specifically activated T lymphocytes in a biological sample, specific separation of such cells is not possible either, because this would require initial unambiguous determination thereof.

Frequently, any activated T cell has its individual cytokine program, which is why the entire specific T lymphocytes cannot be determined and isolated by means of well-known methods wherein specific T lymphocytes are detected and isolated on the basis of their cytokine secretion, e.g. according to WO 99/58977.

Furthermore, the well-known methods of isolating living T lymphocytes via cytokine production are disadvantageous in that the cells are taken out of the culture at the time of their maximum secretion output in order to attach a "capturing matrix" specific for the respective cytokines. Thereafter, the cells have to be re-cultured for a short period of time, thereby considerably increasing the technical input required to obtain specific T lymphocytes. Specifically in recent years, various publications continued to describe regulatory T lymphocytes (Tr/Treg) defying assignment of well-defined cytokine patterns, i.e., the cells cannot be detected or isolated via cytokine secretion. Moreover, the expression of particular cytokines (e.g. IL-10) crucially depends on the type of in vitro activation that is selected.

Therefore, while a number of biomolecules are known which can be used as indicators or markers for particular activated T lymphocytes, current detection and isolation of specific T lymphocytes are also limited by the fact that a decision as to whether the T lymphocytes are in the desired state by determining one of these markers is not possible at present due to the limited number and quality of available activation markers. For example, the activation marker CD69 is expressed by all T lymphocytes following activation. However, any exposure to stress likewise will give rise to expression of CD69, so that determination of said marker does not allow any statement regarding antigen-specific T lymphocytes.

Increased expression of CD154 on CD4+ Th cells as marker for activity of disease in patients with rheumatoid arthritis (RA) is well-known in the prior art (Berner et al., 2000). In this context, the use of CD154 as a specific prognostic or diagnostic marker in a group of patients suffering from RA has been discussed. However, no method for the analysis and/or isolation of antigen-specific T cells has been disclosed or suggested. Such antigen-specific T cells are characterized by a reactivity that is restricted to a defined antigen or a defined mixture of antigens. For example, the publication by Berner et al. discusses the possibility of a long and increased expression of the CD154 molecule on a large number of CD4+ Th cells (average about 45% in the RA CD40L$^{high+}$ group/FIG. 1) which, however, are not characterized by restricted antigen specificity. The authors themselves indicate that CD40L under normal conditions can be detected in a "transient" fashion on activated T cells. As early as in 1998, expression of CD40L on activated T cells has been described by many other groups. However, it is also well-known that the CD40L molecule, following in vitro activation with specific antigens, is no longer available as marker for specific CD4+ Th lymphocytes.

Further, the prior art—e.g. in the publication by Berner et al.—describes the therapeutic application of anti-CD40L antibodies in RA patients. On the basis of animal experimental systems, the general idea of the "antibody therapy" using anti-CD154 antibodies is that administration of anti-CD154 antibody would have an effect on T cell interactions with B cells (suppression of humoral immunity) and with antigen-presenting cells (suppression of chronic inflammation).

According to the prior art, various aspects of the biology of CD154 are known, and the structure, regulation of expression, biological functions and medical applications have been described in detail (Schönbeck et al., 2000).

Schönbeck et al. disclose that expression of CD154 is transient. Furthermore, various polyclonal stimuli capable of inducing CD154 expression on all T cells have been described.

In addition, studies have been reported wherein immunomagnetic reagents for the isolation of monocytes or T cell subpopulations have been used, and isolated fractions of such cells subsequently have been investigated by means of electron microscopy (Fisher et al., 2002).

Part of the signal transduction pathways of the CD40 molecule in B lymphocytes are well-analyzed. Also disclosed are investigations relating to the duration of CD154 expression on T cells. These data have been obtained in experimental systems in which, however, no antigen-specific T cells can be analyzed or isolated in cell mixtures following specific activation with antigens or mixtures of antigens. In contrast, Fisher et al. have described that part of the observed CD154 expression is transient and prolonged only on in vitro generated pro-inflammatory Th1 cells following polyclonal stimulation.

Accordingly, the prior art fails to disclose any methods for the therapeutic use of antigen-specific T cells based on their antigen-reactive CD154 expression.

The object of the present invention is therefore to provide methods allowing easy, economical and reliable detection or isolation of all antigen-specific T lymphocytes, irrespective of their functional potential.

The present invention solves the above technical problem by using CD154 for the detection and/or isolation of T lymphocytes recognizing a particular antigen.

CD154 is a member of the TNF gene family and, inter alia, is expressed by various cells, particularly by T lymphocytes. CD154 is downregulated by the stimulated T lymphocytes one to three hours after activation.

Lymphocytes represent specific carriers of immune response, and two major populations are known: B and T lymphocytes. The T lymphocytes have a large number of surface molecules, amongst which the CD4 and CD8 proteins are of special importance. The CD4 T lymphocytes are also referred to as helper T cells (Th cells) because they aid in the activation of other cells via production of soluble messenger substances.

Lymphocytes and other leukocytes express a wide variety of molecules on their cell surface. Some appear for only a short time during particular phases of differentiation or following activation of the cells. Other molecules are constant and typical of the respective series of cells. Such antigens with constant expression can be utilized as markers for particular cell populations. There is a standardized nomenclature for cell surface markers, i.e., the CD system (CD=cluster of differentiation) wherein the markers are numbered consecutively. Thus, for example, CD154, as well as CD165, or other molecules are present on NK and T lymphocytes.

Surprisingly, CD154 can be used to detect T lymphocytes independently of their functional potential. The surprising advantage of using CD154 in the detection and separation of T lymphocytes is that reliable detection and isolation of T lymphocytes is possible independently of their function, i.e. all antigen-specific T lymphocytes in a sample can be determined and separated. Consequently, the use according to the invention advantageously provides a new practicable candidate for the determination of antigen-specific T lymphocytes.

Accordingly, the teaching disclosed herein also involves the therapeutic use of antigen-specific T cells following isolation based on their antigen-reactive CD154 expression which can be induced after in vitro stimulation with defined antigens or antigen mixtures.

According to a special embodiment of the invention, the T lymphocytes are Th lymphocytes, especially $CD4^+$ and/or $CD8^+$ Th lymphocytes. For antigen recognition, T cell lymphocyte populations utilize a T cell receptor (TCR) which is a heterodimeric molecule consisting of various chain combinations. By far the most T lymphocytes bear an alpha/beta T cell receptor. These T lymphocytes have additional surface molecules, especially the CD4 and CD8 proteins. CD8 lymphocytes are stimulated by antigens presented by MHC class I molecules and, being cytolytic T lymphocytes, they are of crucial importance in virus defense. CD4 T lymphocytes recognize antigens presented by MHC class II molecules and have a substantial part in the defense against bacteria, fungi, protozoa and other parasites.

In another preferred embodiment of the invention, inflammatory, anti-inflammatory, regulatory and/or suppressive T lymphocytes are detected and/or obtained.

The invention also relates to a method for the detection and/or isolation of antigen-specific T lymphocytes in a suspension following activation with an antigen, in which method the suspension is contacted with a CD40/CD154 system inhibitor, intra- and/or extracellular determination of CD154 is effected, and the cells having CD154 are detected and/or isolated.

Surprisingly, such "contacting" with a CD40/CD154 system inhibitor of the suspension or sample to be investigated allows intra- and/or extracellular determination of CD154 and thus, detection and isolation or separation of cells having CD154, said cells in particular representing the entire antigen-specific $CD4^+$ Th lymphocytes.

CD40 is a membrane-bound glycoprotein of the TNF receptor gene family (tumor necrosis factor receptor gene family) and 45 to 50 kDa in size. It is developed by various hematopoietic cell types, but also by epithelial and endothelial cells, carcinomas, fibroblasts, and muscle cells. It can be bound by CD154 which accordingly is a member of the TNF gene family and likewise can be expressed by a large number of cells with highly varying functions. CD40 is expressed on various cells, such as B lymphocytes, dendritic cells, monocytes/macrophages, mast cells, hematopoietic stem/precursor cells (human), thymus epithelial cells (mouse), endothelial cells, fibroblasts (mouse), muscle cells (human) and/or carcinomas (human).

For example, CD154 is expressed on T lymphocytes, activated dendritic cells (human), monocytes, mast cells (human), basophilic/eosinophilic granulocytes (human), NK lymphocytes (mouse), fetal thymocytes (mouse) and/or B cells (human).

In accordance with the highly heterogeneous expression pattern on different cell types, a large number of CD40/CD154 interactions have been described. The CD40/CD154 system is an example of a variety of systems that are based on receptor/ligand interactions and as such have major importance in reactions of the immune system. Inter alia, the CD40/CD154 interactions between T lymphocytes and dendritic cells (DC) are of significance in induction and regulation of the immune response. CD40/CD154 interactions assume a special position in the development of humoral antibody reactions. One special clinical feature involves the so-called X-chromosomal hyper-IgM syndrome—an immune disease wherein expression of a non-functional CD154 gives rise to a massively reduced formation of antibodies and to pyrogenic infections. In other cells, however, the signal transduction via CD40/CD154 also has an influence on thrombus formation in vivo, enhancing the development of arteriosclerosis.

Hence, the importance of CD154 developed by T lymphocytes is essential particularly during the interaction with B lymphocytes to develop humoral antibody responses. It seems that CD154 developed by T lymphocytes is also capable of interacting with CD40 expressed by various antigen-presenting cells (APC). This is obvious because CD154 is rapidly downregulated on activated T lymphocytes during in vitro stimulation with specific antigens. Regarded as responsible for this phenomenon is the interaction of CD154 on activated T lymphocytes with CD40 strongly expressed also by APCs such as monocytes in such systems. The CD154 molecules specifically developed by activated T lymphocytes are subsequently degraded in the cells. In a system not influenced by the method according to the invention, they are no longer available as markers for specific $CD4^+$ Th lymphocytes.

Addition of a CD40/CD154 system inhibitor impairs or inhibits the interaction and signalling between CD40 and CD154. In the meaning of the invention, CD40/CD154 system inhibitors can be any of molecules or even physical exposures capable of blocking or inhibiting the interaction between CD40 and CD154. Accordingly, the inhibiting agent can be an antibody, e.g. one directed against CD40, a molecule, a cesium or lithium ion having an effect on the interaction between CD40 and CD154. Of course, said agent can also be a substance inhibiting the secretion or endocytosis in the cell, such as brefeldin A (Bref-A). Bref-A inhibits the Golgi apparatus and the secretion of a variety of cytokines. These substances ensure that CD40, CD154, the interaction between the two of them, or the CD40/CD154 system are modified in such a way that CD154 either is no longer downregulated and/or degraded on the cell surface, or, provided it is still within the cell, no longer transported therein. Such interruption of the transport within the cell prevents degradation of CD154. Consequently, CD154 is stabilized inside or outside the cell as an external receptor, thereby allowing detection and subsequent isolation using detection methods well-known to those skilled in the art. A person skilled in the art will be familiar with various procedures and devices allowing separation, purification, accumulation or isolation of detected cells of the immune system, e.g. flow cytometry or magnetic cell sorting.

Addition of the CD40/CD154 system inhibitors prevents degradation of CD154 inside and/or outside the cell, so that those cells having CD154 can be characterized and subsequently isolated on the basis of this characterization. Hence, the method according to the invention particularly provides the new, inventive candidate, CD154, for the determination of antigen-specific T lymphocytes.

In a preferred embodiment of the invention, Th lymphocytes, particularly $CD4^+$ and/or $CD8^+$ Th lymphocytes, are detected and/or separated as T lymphocytes.

In a preferred embodiment of the invention, the CD40/CD154 system inhibitor is an antibody directed against CD40, an antibody directed against CD154, a secretion inhibitor and/or an endocytosis inhibitor. A variety of secretion inhibitors and endocytosis inhibitors are known to those skilled in the art. The antibody can be a polyclonal, monoclonal, or a specifically modified antibody, or an antibody fragment, e.g. an antibody associated with a phage or with a phage fragment. The antibody can be directed against a single epitope on CD40 or against a plurality of structures of CD40. An antibody in the meaning of the invention is a molecule affecting CD40 in such a way that interaction with CD154 advantageously is no longer possible. In the context with the invention, antibody therefore means a polypeptide essentially encoded by immunoglobulin genes or fragments thereof, which polypeptide specifically binds or recognizes CD40. The term epitope used in the present invention means any antigen determinant on an antigen to which the paratope of an antibody will bind. More specifically, epitope determinants are constituted of chemically active surface groups of molecules, such as amino acids or sugar side chains, and normally have specific features relating to the three-dimensional structure, as well as specific features relating to the charge.

In a preferred embodiment of the invention, brefeldin A and/or monsensin are used as secretion inhibitor and/or endocytosis inhibitor. Brefeldin A is a metabolite of the fungus *Penicillium brefeldianum* and, being a carboxylated ionophor, blocks the transport of newly synthesized proteins from the endoplasmatic reticulum into the Golgi apparatus and impairs the exchange between endosomes and lysomes, while the circulation between cell membrane and endosomes advantageously remains undisturbed.

In another, particularly preferred embodiment of the invention, the detection of CD154 is intracellular in fixed cells. Since CD154 in an extracellular environment undergoes rapid downregulation or degradation once antigen-specific activation of Th lymphocytes in particular has taken place, intracellular in vitro detection of CD154 with high precision can be effected with advantage. In particular, the transport of the CD154 protein to the cell surface is blocked by adding brefeldin A. Advantageously, this permits analysis of the entire intracellular CD154 in a highly specific manner, thus allowing virtually complete detection of any reactive $CD4^+$ Th lymphocytes in particular. The intracellular determination of CD154 achieves a very good signal-to-noise ratio, thereby enabling extremely reliable and efficient determination of antigen-specific Th lymphocytes.

In another preferred embodiment of the invention, detection of CD154 is extracellular on vital cells. More specifically, in order to employ antigen-specific $CD4^+$ and/or $CD8^+$ Th lymphocytes in the therapeutical or clinical sectors, detection of the cells must be effected in such a way that their functionality is not adversely affected, i.e., in a way that detection is advantageously designed so as to allow detection of living and vital cells to be used subsequently in the production of drugs. For example, it is possible to neutralize CD40 by means of anti-CD40 anti-bodies so as to prevent degradation of CD154 on the cell surface, thereby allowing detection and isolation of antigen-specific $CD4^+$ and/or $CD8^+$ Th lymphocytes.

In a preferred fashion, the antigen-specific T lymphocytes, especially $CD4^+$ and/or $CD8^+$, are obtained from fresh blood, frozen cells, peripheral blood mononuclear cells (PBMC) and/or other body fluids.

In a preferred embodiment of the invention, the isolated and/or separated T lymphocyte cells are those which do not produce any cytokines or do not have a defined cytokine pattern. Advantageously, it is possible to detect and/or isolate any antigen-specific T lymphocytes directed against a particular antigen, i.e. the entire cell population thereof, irrespective of whether or not these T lymphocytes produce cytokines or whether the T lymphocytes defy assignment to a defined cytokine pattern.

In a preferred embodiment of the method according to the invention, inflammatory, anti-inflammatory, regulatory and/or suppressive T lymphocytes are detected and/or isolated and used in cellular therapies for preventive or causal treatment of infectious, allergic, inflammatory, malignant and/or autoimmune diseases.

In another preferred embodiment, inflammatory, anti-inflammatory, regulatory and/or suppressive T lymphocytes are detected and/or isolated and used in cellular therapies for preventive or causal treatment of diseases, said diseases being selected from the group comprising rheumatoid arthritis, multiple sclerosis, systemic lupus erythematosus, scleroderma, vasculitides, reactive arthritis, ankylosing spondylitis, uveitis, Morbus Crohn and/or diabetes.

The inventive method for the detection and isolation of antigen-specific T lymphocytes, e.g. $CD4^+$ Th lymphocytes, permits the use of antigen-specific Th lymphocytes, in particular, in cell therapy against various diseases, such as cancer or viral infections. To date, e.g. Th lymphocytes have been used in the form of cell lines or cell clones in adoptive Th lymphocyte therapy. However, the production of such cell lines or cell clones is highly complex, requiring a long period of time. Using detection of CD154, the method according to the invention permits short-term in vitro and in vivo detection and isolation of antigen-specific Th lymphocytes for the first time. Therefore, selection of Th lymphocytes on the basis of their antigen reactivity and independently of their phenotype is possible for the first time.

The teaching of the invention describes analytical or therapeutical methods, the basis of which being CD154 expression on antigen-specific T cells following stimulation in the presence of a CD154-CD40 system inhibitor. In the teaching that is claimed the induction of CD154 expression after stimulation with antigens or mixtures of antigens is not polyclonal on all T cells, but is selective on T cells with uniform, well-defined antigen specificity. Systems with polyclonal stimulation using lectins, concavalin A, phorbol esters, cytokines or other antibodies as described by Schönbeck et al. permit activation of T cells in the absence of cells presenting antigens. In the method according to the invention, cells expressing antigen-presenting MHC molecules are essential in order to induce physiological stimulation of specific T cells only. The method according to the invention is used in the analysis and isolation of antigen-specific T cells, magnetic cell sorting being one possible technique of separating, purifying, accumulating or isolating the detected cells of the immune system.

By using CD154 as marker for antigen-specific T lymphocytes, it is possible with advantage to obtain specific T lymphocytes, e.g. from body fluids or artificial cell suspensions, against a selected antigen or selected antigens, especially for cell-therapeutic uses. Advantageously, it is possible to isolate specific T lymphocytes for expansion or with subsequent or direct adoptive transfer, said specific T lymphocytes representing inflammatory or anti-inflammatory, particularly regulatory or suppressive T lymphocytes.

Without intending to be limiting, the invention will be illustrated with reference to the following examples.

EXAMPLE 1

Figure 1:
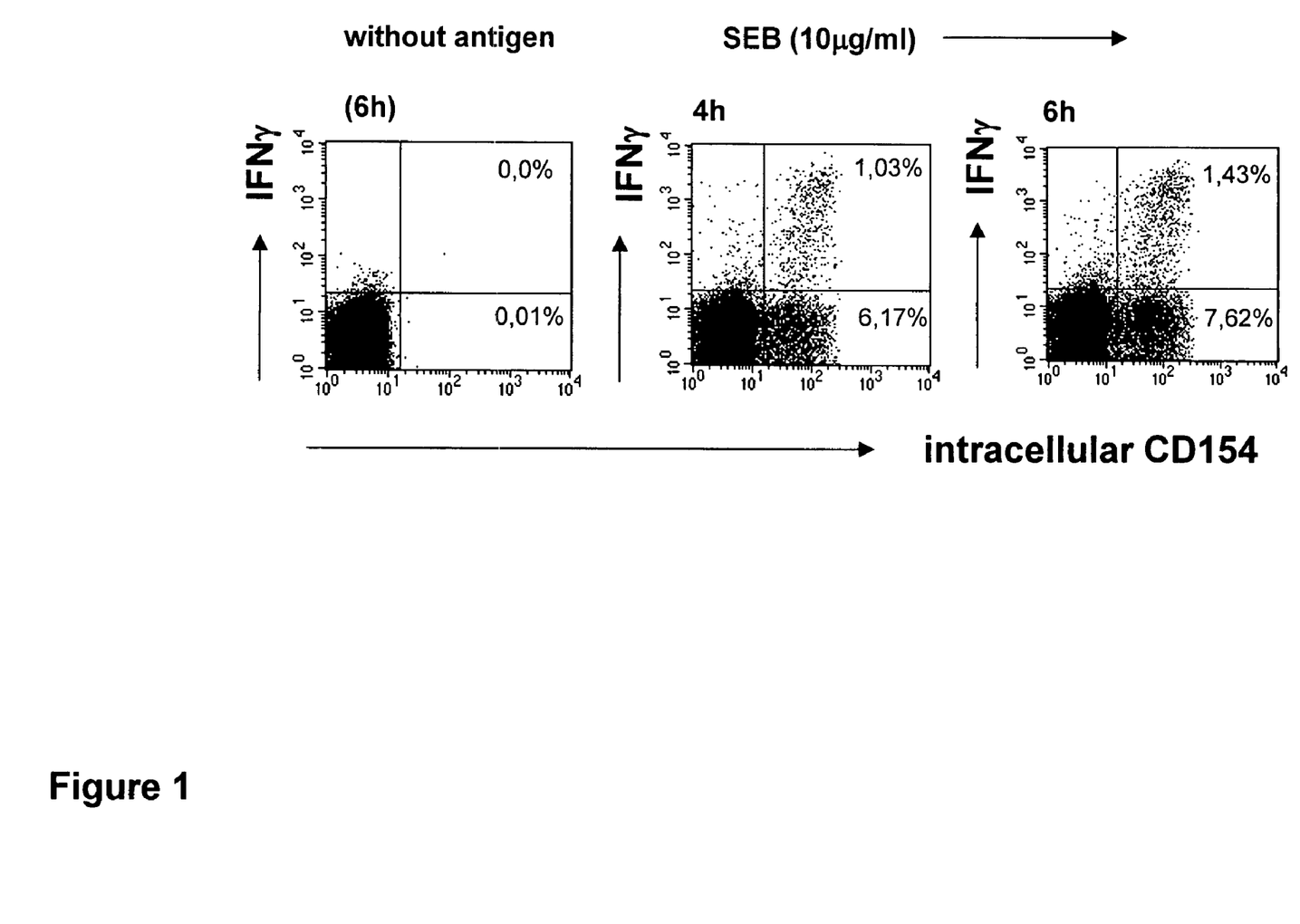
FIG. 1 shows kinetics of intracellular CD154 expression, as determined in antigen-reactive Th cells following in vitro stimulation of human whole blood using the superantigen staphylococcus enterotoxin B (SEB).

The kinetics of intracellular CD154 expression in antigen-reactive Th cells following in vitro stimulation of human whole blood using the superantigen *staphylococcus* enterotoxin B (SEB) was determined. 1 ml of whole blood from a normal, healthy donor was cultured with or without SEB (1 μg/ml) at 37° C. for periods of time as indicated. The secretion inhibitor Bref A was added for the last 2 hours of culturing. Analyses limited to CD4+ Th cells are shown. FIG. 1 shows the kinetics of intracellular CD154 expression.

EXAMPLE 2

Figure 2:
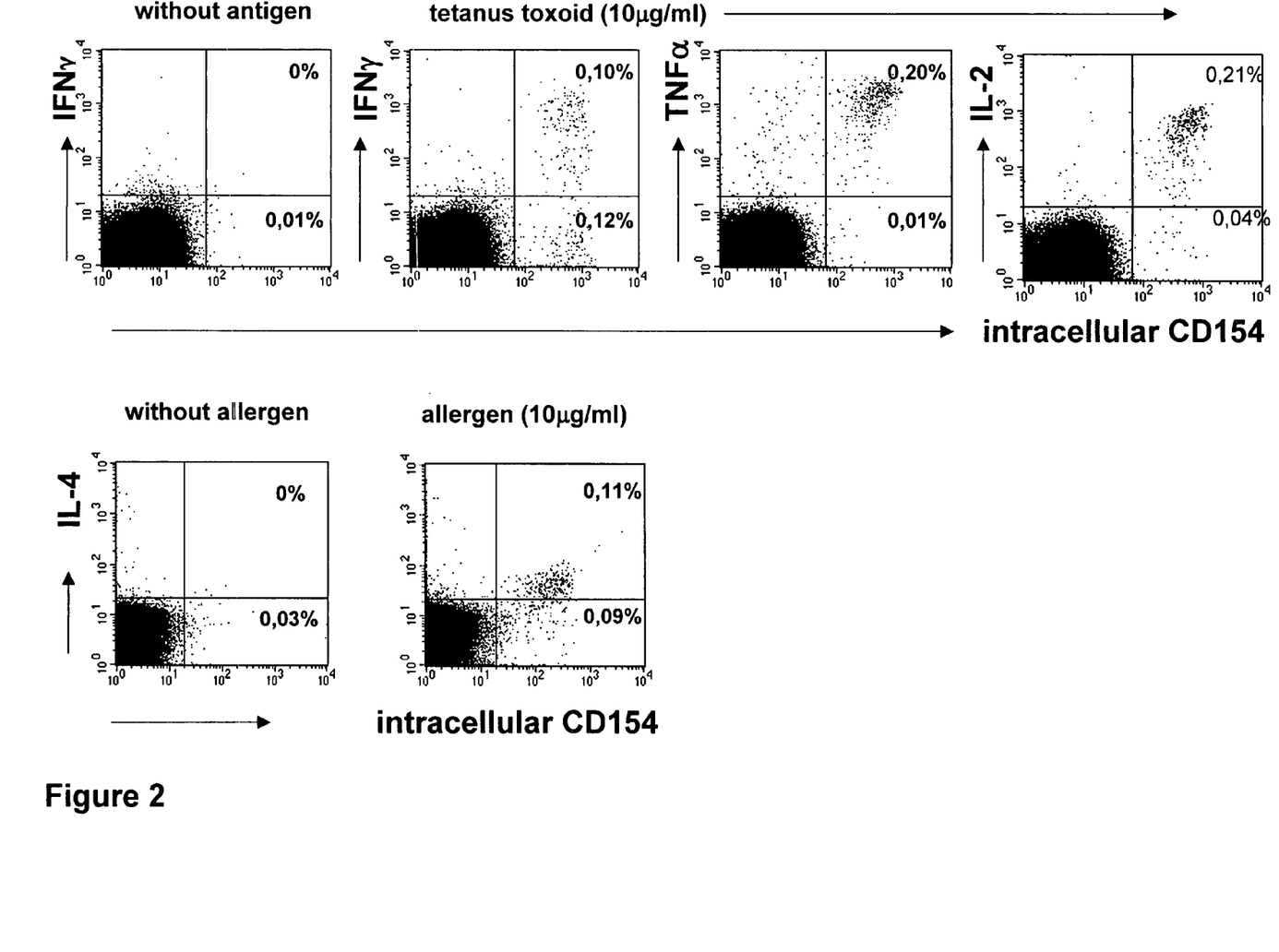
FIG. 2 shows the detection of tetanus toxoid (TT)-specific Th cells and allergen-specific Th cells in human whole blood, independent of the type of reactively produced cytokines after in vitro stimulation with TT and allergen.

FIG. 2 shows the detection of tetanus toxoid(TT)-specific Th cells and allergen-specific Th cells in human whole blood, independent of the type of reactively produced cytokines after in vitro stimulation with TT and allergen. 1 ml of whole blood from healthy donors was cultured with or without the specified antigens (TT: 10 μg/ml/allergen: 20 μg/ml) at 37° C. for 6 hours. The secretion inhibitor Bref A was added for the last 4 hours. Analyses limited to CD4+ Th cells are shown.

EXAMPLE 3

Figure 3:
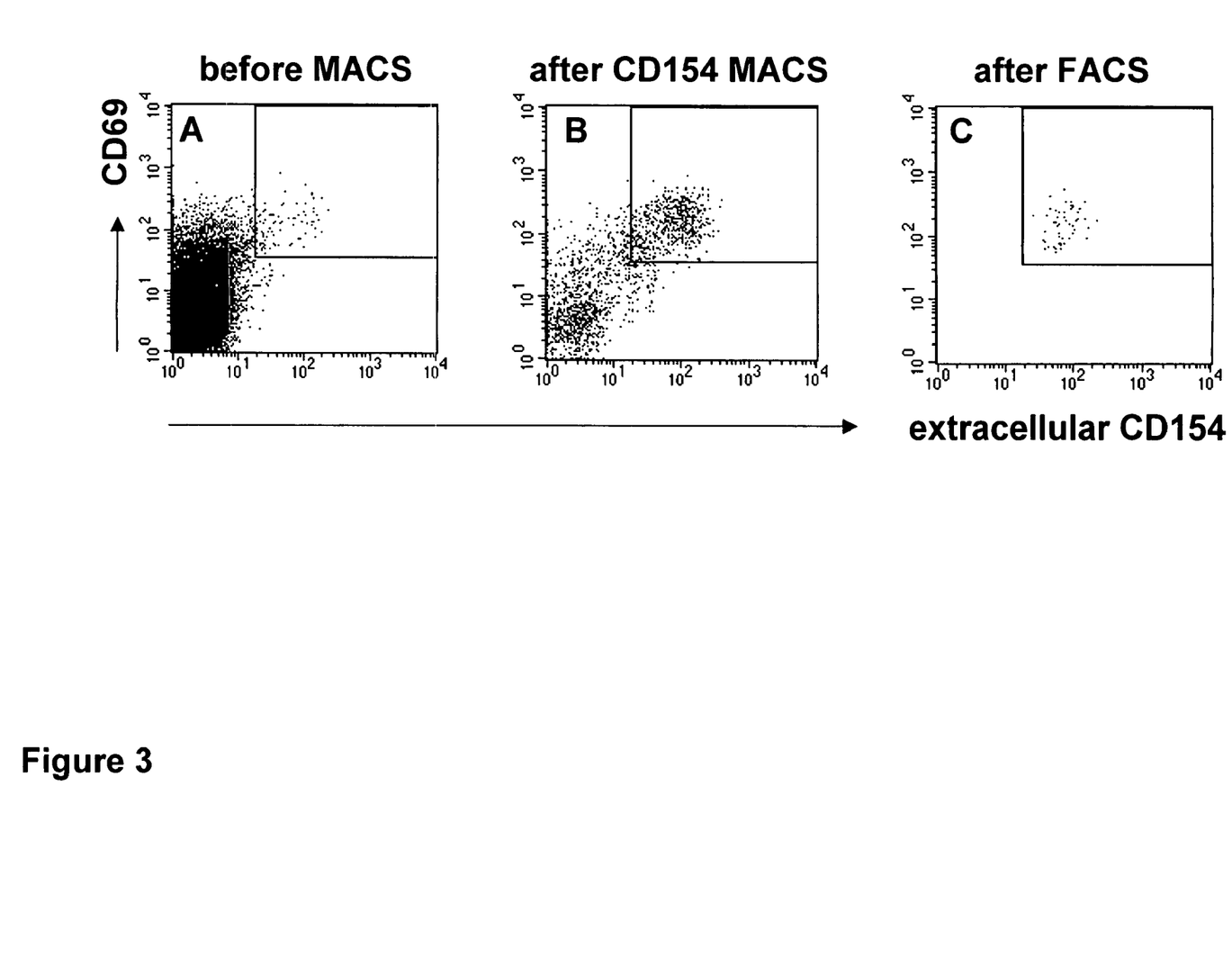
FIG. 3 shows the isolation of living tetanus toxoid (TT)-specific Th cells, based on reactive CD154 expression, from human peripheral mononuclear cells after in vitro stimulation with TT.

The isolation of living tetanus toxoid(TT)-specific Th cells, based on reactive CD154 expression, from human peripheral mononuclear cells after in vitro stimulation with TT is illustrated in FIG. 3. The peripheral mononuclear cells were obtained from about 20 ml of whole blood and cultured for 6 hours with 10 μg/ml TT in the presence of a monoclonal anti-CD40 antibody at 37° C. All samples were labelled with antibodies against CD4-FITC, CD69-APC and CD154-PE. Propiclium iodide was used to exclude dead cells. FIG. 3A shows analyses of the CD154 expression in relationship to the expression of CD69 activation marker prior to isolation. Following magnetic accumulation with PE-specific MICROBEADS (3B), living CD4+, CD154+ Th cells were further purified using FACS (FIG. 3C). In FIGS. 3A and 3B, the analyses are limited to CD4+ Th cells.

Without intending to be limiting, the potential applications of the invention will be emphasized with reference to additional examples.

EXAMPLE 4

The invention permits screening for T cell reactivity using antigens or antigen mixtures. To this end, cells in body fluids can be incubated in vitro with the antigens or antigen mixtures for a short time under suitable conditions, either directly or following processing into mononuclear cells, to be subjected to cytometric analysis of reactive CD154 expression after fixing. On the one hand, this procedure can be utilized in concomitant investigations during vaccination studies, or, on the other hand, in basic research in order to define previously non-defined immunorelevant antigens. In both applications, it is highly important that the application, on the one hand, allows complete detection of the specific, antigen-reactive T cells (especially CD4+ Th cells) and, on the other hand, is independent of previously defined immunodominant peptide epitopes of the antigen or of subject-specific reagents to be produced in the run-up of such investigations.

EXAMPLE 5

The application permits evaluation of antigen-specific T cells with a wide variety of functions. These can be inflammatory T cells characterized by reactive expression of e.g. IFNγ, TNFα or IL-2, anti-inflammatory T cells characterized by reactive expression of e.g. IL-4, IL-5 or IL-13, but also, regulatory T cells characterized by antigen-reactive expression of IL-10 or TGFβ. Furthermore, the method also detects T cells which cannot be characterized by the expression of specific cytokines. In addition to uses in basic research, the method can therefore provide complete evaluation of immune responses in a variety of clinical situations, such as infections with viruses, bacteria or other pathogens, or in the analysis of immune responses against tumor or leukemia antigens. Furthermore, it is also possible to analyze T cells that are involved in allergic reactions or play a crucial role in immunopathological situations such as GvHD or GvL. Ultimately, the method permits direct analysis of regulatory T cells for the first time, especially of so-called natural T "regulatory" cells, the characterization of which is only possible at present via the expression of the transcription factor foxp3 and in part via increased expression of the CD25 molecule.

EXAMPLE 6

In addition, the application permits isolation of antigen-specific T cells for further functional investigations and, for clinical applications, in living condition. Inter alia, clinical applications include adoptive therapies using specific T cells for causal specific therapy in infections with viruses, bacteria or other pathogens, in tumor, leukemia or other malignant diseases, in allergies, autoimmune diseases or other immunomediated diseases such as GvHD or GvL. The preconditions are favorable because the application permits isolation of the entire specific T cells against immunogenic peptides, antigens or mixtures of antigens.

EXAMPLE 7

More specifically, the application complies with the precondition of allowing isolation of autoantigen-specific T cells from complex cell mixtures. In patients already having "established" autoimmune diseases, such cells could be isolated from body fluids such as peripheral blood via their reactive CD154 expression after in vitro stimulation with autoantigens relevant in the respective autoimmune diseases. Following expansion, the cells obtained could be re-infused into the patient. In this way, specific suppression of autoimmune reactions and thus, causal therapy, would be possible for the first time. Inter alia, diseases possibly curable in this way include diseases such as rheumatoid arthritis, multiple sclerosis, systemic lupus erythematosus, scleroderma, vasculitides, reactive arthritis, ankylosing spondylitis, uveitis, Morbus Crohn.

The application can also be utilized in prophylactic therapy, using specific regulatory T cells from risk group patients, in diseases such as diabetes or autoimmune diseases as already mentioned above.

EXAMPLE 8

Furthermore, the application permits analysis of antigen-specific T cells even in non-human species or isolation of such specific T cells from complex cell mixtures for other purposes or investigations. Consequently, the application is not limited to research on human cells, but can also be employed in animal models, using e.g. suitable species-specific reagents, e.g. in monkeys to investigate infectious diseases such as HIV. In addition, the application can be used for ex vivo evaluation of defined immune responses or for the isolation of specific T cells in animal experimental systems such as mouse or rat.

We claim:

1. A method for the detection of antigen-specific T lymphocytes, comprising
    activating said T lymphocytes with an antigen;
    blocking or inhibiting the interaction between CD40 and CD154 with an anti-CD40 antibody or an anti-CD154 antibody; and
    detecting the expression of CD154 on T-lymphocytes using an antibody directed against CD154.

2. The method according to claim 1, comprising detecting $CD4^+$ or $CD8^+$ T lymphocytes which express said CD154.

3. The method according to claim 1, wherein the detected T lymphocyte cells comprise inflammatory, anti-inflammatory, regulatory or suppressive T lymphocytes which express said CD154.

4. A method for the isolation of antigen-specific T lymphocyte cells in a suspension, comprising
    activating said T lymphocytes with an antigen;
    blocking or inhibiting the interaction between CD40 and CD154 with an anti-CD40 antibody or an anti-CD154 antibody; and
    determining intracellular or extracellular CD154 expression on T lymphocytes with an antibody directed against CD154 antibody; and
    isolating T-lymphocyte cells having CD154.

5. The method according to claim 4, comprising isolating $CD4^+$ or $CD8^+$ T lymphocytes which express said CD154.

6. The method according to claim 4, comprising detecting said intracellular or extracellular CD154 levels in or on vital cells.

7. The method according to claim 1, comprising detecting the expression of CD154 with a CD154-specific monoclonal antibody.

8. The method according to claim 1, further comprising detecting T lymphocytes as antigen specific by determining that said T lymphocytes exhibit a higher expression of said CD154 following activation compared to a control population of T lymphocytes that have not been activated.

9. The method according to claim 4, further comprising isolating said T lymphocytes which exhibit a higher expression of said CD154 following activation compared to a control population of T lymphocytes that have not been activated.

10. The method according to claim 1, wherein the antibody is a monoclonal antibody, a polyclonal antibody, an antibody fragment which specifically binds to said CD154, a specifically modified antibody or an antibody associated with a phage or a fragment of said phage-associated antibody.

11. The method according to claim 4, wherein the antibody is a monoclonal antibody, a polyclonal antibody, an antibody fragment which specifically binds to said CD154, a specifically modified antibody or an antibody associated with a phage or a fragment of said phage-associated antibody.

12. The method according to claim 1, wherein the anti-CD40 antibody or the anti-CD154 antibody prevents lowering of the expression of said CD154 on said T lymphocytes.

13. The method according to claim 1, wherein the T lymphocytes are provided in a cell suspension.

14. The method according to claim 1, wherein the anti-CD40 antibody or the anti-CD154 antibody prevents degradation of said CD154 on said T lymphocyte.

15. The method according to claim 4, wherein the anti-CD40 antibody or the anti-CD154 antibody prevents degradation of said CD154 on said T lymphocyte.

16. The method according to claim 4, wherein the anti-CD40 antibody or the anti-CD154 antibody prevents the lowering of the expression of said CD154 on said T lymphocytes.

* * * * *

UNITED STATES PATENT AND TRADEMARK OFFICE
CERTIFICATE OF CORRECTION

PATENT NO. : 7,659,084 B2  Page 1 of 1
APPLICATION NO. : 10/525238
DATED : February 9, 2010
INVENTOR(S) : Frentsch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 795 days.

Signed and Sealed this

Twenty-eighth Day of December, 2010

David J. Kappos
*Director of the United States Patent and Trademark Office*